United States Patent [19]

Nakai et al.

[11] Patent Number: 5,098,700

[45] Date of Patent: Mar. 24, 1992

[54] FAR INFRARED RAY EMITTING, ODOR-ABSORBING MATERIAL

[75] Inventors: Hirotaka Nakai, Kyoto; Setsuji Edagawa, Nishinomiya, both of Japan

[73] Assignee: O.K. Trading Co., Ltd., Osaka, Japan

[21] Appl. No.: 419,941

[22] Filed: Oct. 11, 1989

[30] Foreign Application Priority Data

Jul. 19, 1989 [JP] Japan .................... 1-184710

[51] Int. Cl.$^5$ .................... A61L 9/01; C09K 9/00; D06M 101/08; D06M 11/79
[52] U.S. Cl. .................... 424/76.1; 428/393; 428/384; 428/387; 428/383; 428/386; 428/396; 428/378; 250/504 R; 250/493.1; 250/494.1; 250/495.1
[58] Field of Search ............... 424/76.1; 428/393, 384, 428/387, 913

[56] References Cited

U.S. PATENT DOCUMENTS

| | | | |
|---|---|---|---|
| 3,767,458 | 10/1973 | Moore, Jr. | 428/404 |
| 4,289,513 | 9/1981 | Brownhill | 428/331 |
| 4,396,026 | 8/1983 | Grossman | 131/333 |
| 4,886,972 | 12/1989 | Nakai et al. | 250/493.1 |

FOREIGN PATENT DOCUMENTS 0184926 6/1986 European Pat. Off. .

OTHER PUBLICATIONS

Table, Chemical Engineering, Jun. 11, 1962 p. 207.

*Primary Examiner*—Thurman K. Page
*Assistant Examiner*—E. J. Webman
*Attorney, Agent, or Firm*—Oblon, Spivak, McClelland, Maier & Neustadt

[57] ABSTRACT

A far infrared ray emitting, odor-absorbing material is disclosed. The material comprises cellulose acetate fiber having adhered thereto an ultrafine powder of alumina hydrate or silica hydrate which is chemically produced in an aqueous dispersion of the cellulose acetate fiber. The material possesses a high far infrared ray emitting, odor-absorbing capability as well as many characteristics inherently possessed by cellulose acetate fibers, and can expand the utility of cellulose acetate in such fields as sanitary, health-care, and medical fields.

2 Claims, No Drawings

FAR INFRARED RAY EMITTING, ODOR-ABSORBING MATERIAL

BACKGROUND OF THE INVENTION

1. Field of the Invention

This invention relates to a far infrared ray emitting, odor-absorbing material which is made of cellulose fiber, especially of cellulose acetate fiber, and an inorganic core material having adhered thereto an ultrafine powder of alumina hydrate or silica hydrate which is chemically produced in an aqueous dispersion of said inorganic core material.

2. Description of the Background

Fiber products including textiles, lace, knits, nonwoven fabrics, felts, etc. are used mostly as clothing materials. Fibers are spun into strands or yarns by spinning processes, and are woven into textiles, knitted into knitting goods, packed and adhered into nonwoven fabrics, or otherwise processed to produce other fiber products.

Fibers from which textiles or yarns are prepared are called spinning and weaving fibers. Among the spinning and weaving fibers, those prepared into the clothing materials are called clothing fibers. Spinning and weaving fibers are broadly classified into naturals fibers, such as the fibers of vegetable, animal, or mineral origin, and synthetic fibers.

Synthetic fibers are grouped into inorganic fibers, (e.g. glass or ceramic fibers), those in the rayon family, and the synthetic fibers produced from substances derived from petroleum (e.g. nylon, polyester, acrylic fibers, etc.).

Fibers of the rayon family are of two types. One is those made from regenerated cellulose (wood pulp). Viscose and cuprammonium belong to this group. Both are derived from wood pulp dissolved in caustic soda. The other type is cellulose acetate fibers which are the reaction products (esters) of acetic acid and cellulose. Depending on the degree of acetylation cellulose acetate fibers are grouped into diacetate (usually called simply "acetate") and triacetate.

Triacetyl cellulose is produced by the reaction of acetic anhydride and cellulose. All three hydroxyl groups in glucose recurring units in cellulose are esterified by acetic acid in triacetyl cellulose. Triacetate is produced by dissolving the triacetyl cellulose into a suitable solvent, typically into a mixed solvent of methylene chloride and methanol, and by forcing the solution through spinnerets. Diacetyl cellulose is produced by adding water to triacetyl cellulose and heating the mixture to hydrolyze. The product is dissolved into acetone and the solution is spun to produce diacetate (or acetate). Acetate fabrics are known for their brilliance of color and ability to drape well, properties that have made them particularly successful as apparel fabrics. Triacetate yarns have many of the same properties as diacetate but are particularly known for their ability to provide pleat retention in apparel. Short fibers (staples) of cellulose acetate are used as filling materials in pillows, mattress pads, and quilts and also as filtering agent of cigarettes. They are very frequently used blended with other fibers.

In contrast to natural fibers and synthetic fibers having round, circular cross sections, the cross sections of acetate and triacetate fibers are concaved circles like leaves of clover. This makes the specific surface area of cellulose acetate fibers large.

Despite the above characteristics, cellulose acetate fibers do not possess a far infrared ray emitting, heat-retaining property or a deodorizing effect which are demanded of fibers used for sanitary, health-care, or medical purposes.

The present inventors had previously developed a far infrared ray emitting body comprising a base material or an inorganic core material having an ultrafine inorganic powder with a closely distributed particle size adhered on said base or core material, and filed an application for patent (U.S. application Ser. No. 07/296,026 now U.S. Pat. No. 4,886,972). Specifically, the invention comprised a core material having adhered thereto an ultrafine powder of a particle size below 500 angstrom of one or more compounds selected from the group consisting of alumina hydrate, silica hydrate, and the mixture thereof which is chemically produced in an aqueous dispersion of said core material.

The further studies by the inventors were directed to applications of the far infrared ray emitting body. As a result the inventors found that by the combination of the far infrared ray emitting body and cellulose acetate fibers provides the latter with a superior far infrared ray emitting, heat-retaining characteristics as well as a superb deodorizing effect. This finding has led to the completion of the present invention.

SUMMARY OF THE INVENTION

Accordingly an object of this invention is to provide a far infrared ray emitting, odor-absorbing material, comprising:

an inorganic core material having adhered thereto an ultrafine powder of a particle size below 500 angstrom of one or more compounds selected from the group consisting of alumina hydrate, silica hydrate, and the mixture thereof which is chemically produced in an aqueous dispersion of said inorganic core material; and cellulose acetate fiber in which said inorganic core material having adhered thereto an ultrafine powder is filled.

Another object of the present invention is to provide a far infrared ray emitting, odor-absorbing material, comprising:

cellulose acetate fiber having adhered thereto an ultrafine powder of a particle size below 500 angstrom of one or more compounds selected from the group consisting of alumina hydrate, silica hydrate, and the mixture thereof which is chemically produced in an aqueous dispersion of said cellulose acetate fiber.

A still further object is to provide a far infrared ray emitting, odor-absorbing material, comprising:

(i) cellulose acetate fiber and (ii) one or more inorganic core materials selected from the group consisting of naturally occurring clay minerals, synthetic inorganic compounds, and synthetic pigments, both (i) and (ii) having adhered thereto an ultrafine powder of a particle size below 500 angstrom of one or more compounds selected from the group consisting of alumina hydrate, silica hydrate, and the mixture thereof which is chemically produced in an aqueous dispersion of said cellulose acetate fiber, and wherein said one or more inorganic core materials having adhered thereto said ultrafine powder is filled in said cellulose acetate fiber.

Other objects, features and advantages of the invention will hereinafter become more readily apparent from the following description.

DETAILED DESCRIPTION OF THE INVENTION AND PREFERRED EMBODIMENTS

The inorganic core material used in this invention may be selected from a wide variety of materials. It may be a naturally occurring clay mineral such as kaolin, mica, or silicate; a synthetic inorganic compound such as alumina or silica; a synthetic pigment such as zirconia or titania. Given as more specific examples of the material which can be used as an inorganic core material in this invention are thin-layered minerals such as kaolin, vermiculite, mica, and the like; spherical particles such as spherical silica, beryllium, and the like; fibrous material such as glass fibers, ceramic fibers, carbon fibers, zeolite fibers, and the like; porous material such as zeolite, diatomaceous earth, and the like; pigments, including various oxides, carbonates, sulfates, and nitrates, such as zirconia, titanium white, zinc white, barium titanate, and the like; and films such as plastic films.

Ultrafine inorganic particles in this invention are formed in an aqueous dispersion of inorganic core material by adding inorganic compounds which can produce by reaction such inorganic particles. Preparation of such ultrafine inorganic particles is described in the pending U.S. patent application Ser. No. 07/152,853 by the present inventors. Specifically, particles may be those of alumina hydrate or silica hydrate formed by a chemical reaction in an aqueous dispersion of inorganic core materials. A typical example of a fine particulate inorganic material is alumina hydrate produced by the reaction of aluminum chloride and ammonium hydroxide. Other examples of such fine particulate inorganic materials are silica, silicate, and the like. For example, to an aqueous solution of aluminum chloride an equivalent amount of ammonium hydroxide to neutralize the aluminum chloride is added to obtain alumina hydrate. In this instance, fine particles of the inorganic material, e.g. alumina hydrate in this case, deposit in the aqueous dispersion system. Needle-like alumina hydrate deposits and adheres on the surfaces of the suspended inorganic core material to form a film, thus producing an ideal uneven surface with a large specific surface area which can provide a significant far infrared radiation effect.

Hydrate of alumina or silica takes the form of ultrafine particles having a size of 500 angstrom or below, preferably 200 angstrom or below. The ultrafine particles remain unagglomerated in the dispersion and adhere on and evenly cover the surfaces of inorganic core materials to produce a reformed material with a uniform silica or alumina coat. Taking a reformed kaolin (a core material) covered with alumina hydrate, as an example, when water is eliminated and the material is dried, this material has a very uniformly aligned kaolin-alumina hydrate-kaolin structure, which is not seen with a mere mixture of kaolin and alumina. It is impossible to prepare alumina hydrate particles of a 100 to 200 angstrom size by any other means. Sizes on the order of 3,000 angstrom are considered to be an ultrafine aluminum particle size according to the present technological level. Besides silica and alumina, other inorganic compounds can be used as the covering ultrafine powdery material of this invention, so long as such compounds can be prepared by the reaction of a soluble acid and a soluble alkali. Examples of such compounds are carbonates of calcium, magnesium, barium, and the like.

The far infrared ray emitting, odor-absorbing material of the present invention can be prepared by filling the far infrared ray emitting body thus prepared into cellulose acetate fibers. As previously mentioned, since cellulose acetate fibers have a clover-shaped, concaved circular cross section and have a large specific surface area, there are ample spaces in the cellulose acetate fibers into which fine particles of far infrared ray emitting body can be filled. The fill-out operation can be performed by any suitable method. A simple way of filling is to blend prescribed amounts of far infrared ray emitting particles and cellulose acetate fibers. A ratio of far infrared ray emitting particles and cellulose acetate fibers to be blended is usually 1-50 parts by weight of far infrared ray emitting particles per 100 parts by weight of cellulose acetate fibers, with a preferable range being 1-10 parts by weight of far infrared ray emitting particles per 100 parts by weight of cellulose acetate fibers.

The far infrared ray emitting, odor-absorbing material of the present invention can also be prepared by using, instead of above-mentioned inorganic materials, cellulose acetate fibers as core materials in the preparation of the far infrared ray emitting body. In this instance, a proportion of ultrafine particles of hydrate of alumina or silica and cellulose acetate fibers is 1-50 parts by weight of the former per 100 parts by weight of the latter.

Another alternative method of preparing the far infrared ray emitting, odor-absorbing material of the present invention is to add cellulose acetate fibers to the aqueous dispersion of inorganic core materials in which ultrafine particles of alumina hydrate or silica hydrate is formed by a chemical reaction. A proportion of the components to be used for 100 parts by weight of cellulose acetate fibers are 1-100 parts by weight of inorganic core materials and 1-50 parts by weight of ultrafine particles of alumina hydrate or silica hydrate.

Any fibers other than cellulose acetate fibers can be used mixed with cellulose acetate fibers.

Materials prepared according to the above procedures have ultrafine particles of alumina hydrate or silica hydrate having a large specific surface filled in cellulose acetate fibers which also have a large specific surface area. The material has excellent far infrared ray emitting, odor-absorbing effects and can expand the fields in which cellulose acetate fibers can be used.

Other features of the invention will become apparent in the course of the following description of the exemplary embodiments which are given for illustration of the invention and are not intended to be limiting thereof.

EXAMPLE 1

Ten (10) kg of silicic acid hydrate (manufactured by OK Trading Co., Ltd.) having an average particle size of 0.2 $\mu$m was dispersed into 10 m$^3$ of water. To this dispersion, AlCl$_3$ was added in such an amount that alumina hydrate (as Al$_2$O$_3$.3 H$_2$O) of 5 kg could be produced. To this, NH$_4$OH equivalent to neutralize AlCl$_3$ was added to ensure precipitation and adsorption of alumina hydrate of a 100 angstrom size on the surface of silicic acid hydrate. Water was removed from the product by means of a filter press, followed by drying at 100° C. The dried substance was pulverized by hammer to obtain a far infrared ray emitting body. This body was filled in cellulose acetate fiber in an amount of 3% by weight of the cellulose acetate fiber. The fiber was spun to obtain 6 denier far infrared ray emitting, odor-absorbing yarn of this invention.

Example 2

No. 3 water glass containing 3 kg of $SiO_2$ was added to a dispersion of 10 kg of $TiO_2$ (having an average particle size of 0.2 μm) prepared in the same manner as in Example 1. To this mixture HCl in an amount equivalent to neutralize $SiO_2$ was added to produce $TiO_2$ of which surface is reformed by $SiO_2$. An amount of 3% by weight of this material was filled in cellulose acetate fiber in the same manner a in Example 1. The fiber was spun into 6 denier far infrared ray emitting, odor-absorbing yarn of this invention.

Example 3

Hundred (100) kg of cellulose acetate fiber was dispersed into 10 m$^3$ of water. To this dispersion, $AlCl_3$ was added in such an amount that alumina hydrate (as $Al_2O_3.3H_2O$) of 3 kg could be produced. To this, $NH_4OH$ equivalent to neutralize $AlCl_3$ was added to ensure precipitation and adsorption of alumina hydrate of a 50 angstrom size on the surface of cellulose acetate fiber. Water was removed from the product by means of a filter press, followed by drying at 100° C. The dried fiber was spun into 6 denier far infrared ray emitting, odor-absorbing yarn of this invention.

Example 4

No. 3 water glass containing 3 kg of $SiO_2$ was added to a dispersion of 100 kg of cellulose acetate fiber prepared in the same manner as in Example 3. To this mixture HCl in an amount equivalent to neutralize $SiO_2$ was added to produce cellulose acetate fiber of which surface is reformed by film-like $SiO_2$. The fiber was spun into 6 denier far infrared ray emitting, odor-absorbing yarn of this invention.

Example 5

Hundred (100) kg of cellulose acetate fiber and 10 kg of silicic acid hydrate having an average particle size of 0.2 μm were dispersed into 10 M$^3$ of water. To this dispersion, $AlCl_3$ was added in such an amount that alumina hydrate (as $Al_2O_3.3H_2O$) of 3 kg could be produced. To this, $NH_4OH$ equivalent to neutralize $AlCl_3$ was added to ensure precipitation and adsorption of alumina hydrate on the surface of cellulose acetate fiber and silicic acid hydrate. Water was removed from the product by means of a filter press, followed by drying. The dried substance was spun to obtain 6 denier far infrared ray emitting, odor-absorbing yarn of this invention.

Example 6

The procedure of Example 5 was followed, except that $AlCl_3$ used was such an amount that alumina hydrate (as $Al_2O_3.3H_2O$) of 30 kg, instead of 3 kg, could be produced and the amount of $NH_4OH$ used was equivalent to neutralize this $AlCl_3$ to obtain 6 denier far infrared ray emitting, odor-absorbing yarn of this invention.

Example 7

Ten (10]kg of the dried fiber before spinning prepared in Example 3 was blended with 2 kg of polyester fiber and spun into 6 denier far infrared ray emitting, odor-absorbing yarn of this invention.

Example 8

Ten (10),kg of the dried fiber before spinning prepared in Example 3 was blended with 2 kg of silk and spun into 6 denier far infrared ray emitting, odor-absorbing yarn of this invention.

Comparative Example 1

The same cellulose acetate fiber as used in Example 1, without mixing with the far infrared ray emitting body, was spun into 6 denier yarn.

Comparative Example 2

The same silicic acid hydrate and cellulose acetate fiber as used in Example 1 blended at a ratio of 3:97 and the blend was spun into 6 denier yarn.

Comparative Example 3

The far infrared ray emitting body produced in Example 1 was blended with polyester fiber at a ratio of 3:97 and the blend was spun into 6 denier yarn.

Comparative Example 4

The far infrared ray emitting body produced in Example 1 was blended with polypropylene fiber at a ratio of 3:97 and the blend was spun into 6 denier yarn.

Test Examples

Infrared radiation and $NH_3$ deodorizing effect were measured on the products prepared in Examples 1-8 Comparative Examples 1-4 according to the following procedures.

(1) Infrared Radiation

An infrared radiation strength of between 2 μm and 30 μm was measured by using an infrared spectrometer (Type A-302 manufactured by Nippon Bunkokogyo Co., Ltd.) equipped with an auxiliary photometer. The detector plotted a comparative value of each sample against a black body which was used as a standard.

The mean integral value of the far infrared radiation strength between 5 to 15 μm was determined for each sample. Relative strength for each sample was then calculated taking the radiation strength at 5-15 μm of the sample prepared in Example 1 as 100%. [The Shigaraki Ceramic Research Institute (Shiga Prefecture, Japan) Method]

(2) Deodorizing Effect (i) Test samples were prepared by placing the products in a dryer at 110° C. for 3 hours and then allowing the dried products to cool in a desiccator.

(ii) A 12,150 ml glass container was used for ammonia absorption. A magnetic stirrer was provided at the bottom of the container for stirring $NH_3$ gas.

(iii) A Kitazawa Gas Detector (manufactured by Kitazawa Industry Co., Ltd.) was used for measurement of $NH_3$ gas concentrations.

(iv) An ammonia absorption test was performed as follows. A specified amount of a high concentration ammonia gas was injected to the glass container by a microsyringe. After stirring for five minutes the gas concentration in the container was measured by the gas detector. This procedure was repeated several times. One (1) gram of a sample was then placed in the container and the specified amount of a high concentration ammonia gas was injected to the glass container by a microsyringe in the same manner as above. After stirring for 5 minutes the ammonia concentration in the container was measured. Deodorization was calculated from the reduced concentration of ammonia gas.

The results are shown in the following table. Given in the table for reference is $NH_3$ deodorization for coconut shell activated carbon.

|  | Infrared Radiation Relative Strength (5 to 15 μm) | $NH_3$ Deodorization (%) |
| --- | --- | --- |
| Example 1 | 100 | 50 |
| Example 2 | 90 | 45 |
| Example 3 | 120 | 60 |
| Example 4 | 105 | 55 |
| Example 5 | 125 | 65 |
| Example 6 | 130 | 70 |
| Example 7 | 110 | 50 |
| Example 8 | 110 | 55 |
| Comparative Example 1 | 30 | 20 |
| Comparative Example 2 | 50 | 25 |
| Comparative Example 3 | 60 | 40 |
| Comparative Example 4 | 55 | 40 |
| Activated carbon |  | 37 |

The produce of the present invention possesses a high far infrared ray emitting, odor-absorbing capability as well as many characteristics inherently possessed by fibers, especially by cellulose acetate fibers. Thus, the product will enormously expand the utility of cellulose acetate.

Obviously, numerous modifications and variations of the present invention are possible in light of the above teachings. It is therefore to be understood that within the scope of the appended claims, the invention may be practiced otherwise than as specifically described herein.

What is claimed is:

1. A far infrared ray emitting, odor-absorbing material, comprising:
   cellulose acetate fiber having adhered thereto an ultrafine powder having a particle size below 500 angstroms of one or more compounds selected from the group consisting of alumina hydrate, produced by reacting aluminum chloride and ammonium hydroxide, silica hydrate, produced by reacting silicon dioxide and hydrochloric acid, and the mixture thereof, wherein said ultrafine powder is chemically produced in an aqueous dispersion of said cellulose acetate fiber.

2. A far infrared ray emitting, odor-absorbing material, comprising:
   (i) cellulose acetate fiber and (ii) one or more inorganic core materials selected from the group consisting of naturally occurring clay minerals, synthetic inorganic compounds, and synthetic pigments, both (i) and (ii) having adhered thereto an ultrafine powder having a particle size below 500 angstroms of one or more compounds selected from the group consisting of alumina hydrate, produced by reacting aluminum chloride and ammonium hydroxide, silica hydrate produced by reacting silicon dioxide and hydrochloric acid, and the mixture thereof, wherein said ultrafine powder is chemically produced in an aqueous dispersion of said cellulose acetate fiber, and wherein said cellulose acetate fiber is filled with one or more of said inorganic core materials having adhered thereto said ultrafine powder.

* * * * *